United States Patent [19]

Klopfer et al.

[11] Patent Number: 4,954,777
[45] Date of Patent: Sep. 4, 1990

[54] DEVICE FOR DEFECT TESTING OF NON-FERROMAGNETIC TEST SAMPLES AND FOR FERROMAGNETIC INCLUSIONS

[75] Inventors: Walter Klopfer, Mossingen; Fritz Haug, Pliezhausen, both of Fed. Rep. of Germany; Dale Gabauer, Freedom; James Workley, Imperial, both of Pa.

[73] Assignee: Institut Dr. Friedrich Forster Prufgeratebau GmbH & Co. KG, Ruetlingen, Fed. Rep. of Germany

[21] Appl. No.: 282,450

[22] Filed: Dec. 9, 1988

[30] Foreign Application Priority Data

Dec. 22, 1987 [DE] Fed. Rep. of Germany ....... 3743521

[51] Int. Cl.$^5$ ................... G01N 27/82; G01N 27/90
[52] U.S. Cl. ..................... 324/232; 324/227; 324/241
[58] Field of Search ............... 324/227, 232, 239–243

[56] References Cited

U.S. PATENT DOCUMENTS

| | | | |
|---|---|---|---|
| 2,207,592 | 7/1940 | Lenk | 324/239 |
| 3,065,412 | 11/1962 | Rosenthal | 324/239 |
| 3,271,664 | 9/1966 | Mountz et al. | 324/232 X |
| 3,314,006 | 4/1967 | Hentschel | 324/233 |
| 3,391,336 | 7/1968 | Hentschel | 324/233 |
| 3,401,332 | 9/1968 | McClurg et al. | 324/232 X |
| 3,538,433 | 11/1970 | Wood et al. | 324/232 X |
| 3,972,156 | 8/1976 | Bennett, Jr. et al. | 324/243 X |
| 4,303,885 | 12/1981 | Davis et al. | 324/233 X |
| 4,602,212 | 7/1986 | Hiroshima et al. | 324/227 |
| 4,618,823 | 10/1986 | Dahlheimer et al. | 324/232 X |

Primary Examiner—Gerard R. Strecker
Attorney, Agent, or Firm—George J. Netter

[57] ABSTRACT

Detection of both surface defects of a non-ferromagnetic test body as well as the presence of ferromagnetic particles in the test body by inducing eddy currents and D.C. fields in the body. The resulting signal voltages are filtered and separately examined.

1 Claim, 2 Drawing Sheets

DEVICE FOR DEFECT TESTING OF NON-FERROMAGNETIC TEST SAMPLES AND FOR FERROMAGNETIC INCLUSIONS

BACKGROUND OF THE INVENTION

1. Field of the Invention.

The present invention relates generally to the defect testing of non-ferromagnetic materials, and, more particularly, to such testing of semifinished materials.

2. Description of Related Art.

It is known to determine the presence of defects in metal objects by inducing eddy currents in the objects and examining the field produced thereby. Such techniques have been used to test a variety of semifinished materials, such as wire, rods and pipes. In particular, the tests are made after the test samples have undergone a shaping or fashioning, e.g. in a rolling mill or the like, and in this way you can detect cracks, shrink holes, laps, shells and other defects, to the extent they are located immediately under the outer surface of the test sample.

Where ferromagnetic materials are found to be present in a non-ferromagnetic object this indicates defects in the shaping tools, e.g. wearing of rollers and splitting-off of particles which have then been rolled into the semifinished material. On the other hand, inclusions of ferromagnetic material in a test object may give rise to serious results on further processing of the semifinished material, such as splittings, breaks or the like, damaging the drawing tool when drawing semifinished material to smaller and smaller diameters.

The utilization of past known eddy-current methods for the detection of ferromagnetic inclusions in an otherwise non-ferromagnetic body has not been totally satisfactory. First, so-called "skin effect" prevents eddy currents from penetrating deep into the material and even inclusions disposed only slightly underneath the surface are not indicated. It is true that the penetration depth may be slightly improved by lowering test frequency. This is achieved, however, at the cost of the recognition of surface defects and reduces the potential test speed. A second deficiency is based on the fact that, beside the inclusions extending up to the surface, further categories of surface defects are detected, too, by means of the eddy-current test. The relation of the importance of a defect to the respective signal voltage is, however, very different, depending on whether inclusions or other defects are concerned. A definite evaluation of the importance of defects has not been possible in the past, if different categories of defects occur to the same extent.

Another technique is known by which the detection of inclusions of ferromagnetic material in metal semifinished material is possible. For example, if the semifinished material is passed through a coil, in the region of which a strong, constant magnetic field is built up, the ferromagnetic particles passing through the coil act as magnetic dipoles and induce an electrical voltage in the coil.

$$v = n \cdot d\phi/dt, \quad (1)$$

with n being the number of windings of the coil and $\phi$ the magnetic flux penetrating the coil which results from the dipole. Accordingly, the presence of inclusions of ferromagnetic material in metal semifinished material can be detected, however not in the presence of any other surface defects, although the latter might easily be detected by the eddy-current method.

OBJECTS AND SUMMARY OF THE INVENTION

It is, therefore, an object of the invention to provide apparatus for detecting the presence of inclusions of ferromagnetic material as well as the presence of surface defects in metal semifinished material.

The described invention allows utilization of two different physical detecting means in a common device which is accomplished relatively simply. In particular, the test coil arrangement and the means for evaluating the signal voltages may commonly be used for both methods. It is particularly advantageous to be able to use one test coil arrangement only for eddy-current testing as well as for induction testing if integration into an existing production line is concerned, where for space reasons two test coil arrangements would be difficult, if not impossible to accommodate.

According to a first embodiment of the invention, first and second signal voltages representative of ferromagnetic inclusions and defects in the non-ferromagnetic body, respectively, are separated from each other by a low-pass filter, and according to another aspect a common preamplifier is used for the first and second signal voltages. Another embodiment of the invention consists in that as magnetizing means, a magnet yoke is employed which is only energized to achieve magnetic saturation of ferromagnetic test samples.

DESCRIPTION OF THE DRAWINGS

FIGS. 2, 2a and 2b depict the magnetizing yoke with test coil arrangement supported therein.

DESCRIPTION OF PREFERRED EMBODIMENTS

Figure 1:
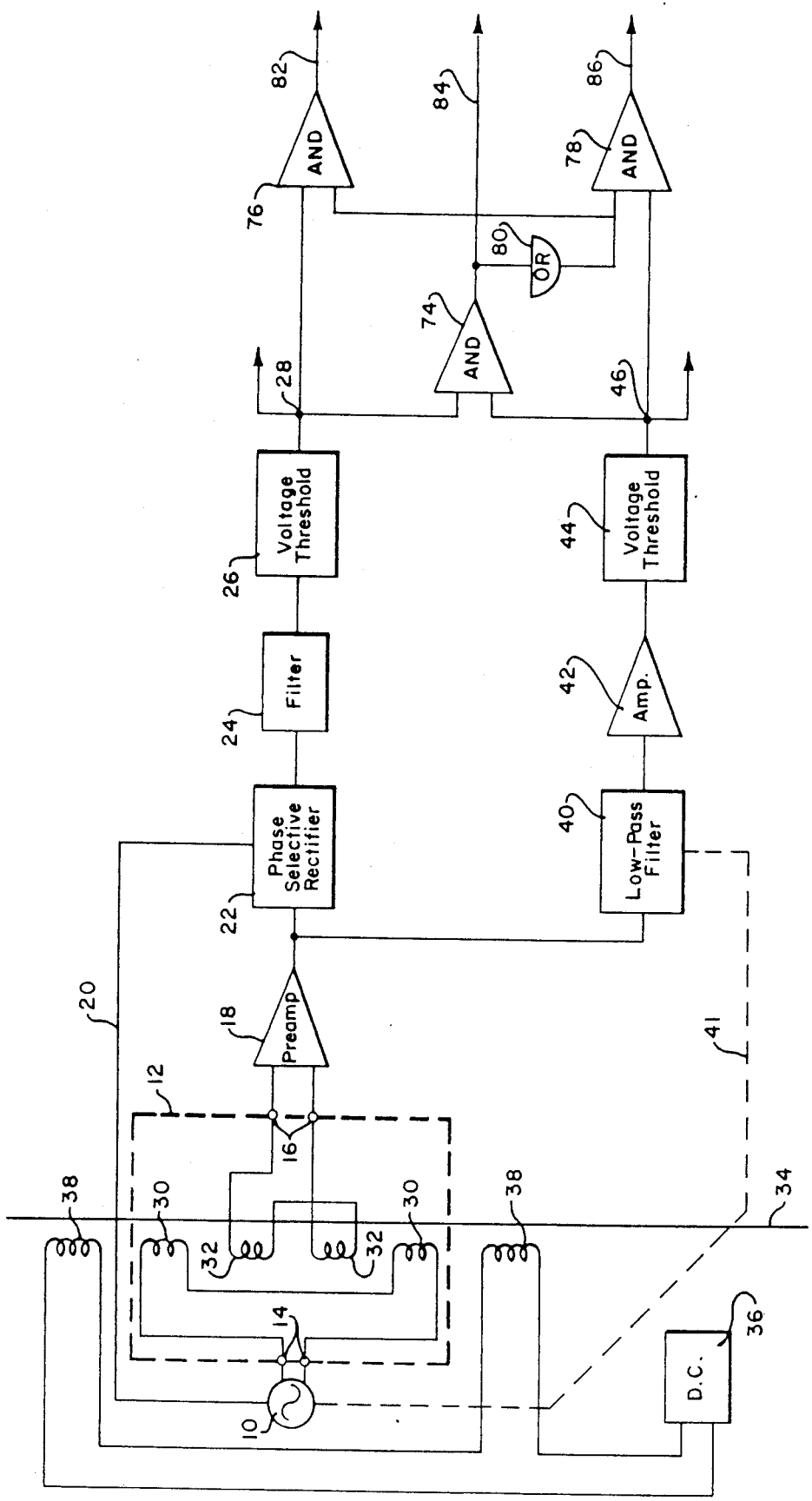
FIG. 1 is a block diagram of the test apparatus of this invention.

In the block diagram of FIG. 1, a device basically known for testing metals according to eddy-current principles is shown. It consists of an eddy-current generator 10 having a selectively variable frequency, a test coil arrangement 12, the given frequency alternating current input 14 to which is supplied by the generator 10. A preamplifier 18 is connected between the output 16 of the test coil arrangement 12 and a phase-selective rectifier 22 controlled by the generator 10 via a conductor 20. The phase-selective rectifier 22 demodulates the signal voltage generated in the test coil arrangement 12 and amplified by the preamplifier 18 after which a filter 24 suppresses undesired components of the signal voltage. A signal voltage threshold stage 26 creates a binary signal at its output when a certain threshold voltage is exceeded by the signal voltage.

The test coil arrangement 12 has two exciter coils 30 and two receiver coils 32 which, in use, are in relative motion with respect to the test sample, shown as a wire 34 of non-ferromagnetic metal. The alternating current flowing in the exciter coils 30 builds up an alternating magnetic field acting on the wire 34 and causing eddy currents therein. The eddy currents, in turn, produce magnetic fields which induce voltages in the receiver coils 34. As coils 34 are connected in series opposition, the voltages induced in them compensate each other, as long as there are no surface defects in the wire 34 to be investigated. Surface defects of the wire 34 on passing through the coil arrangement 12 affect the creation of eddy currents and, therefore, cause voltage changes in the receivers coils 32, which do not compensate each other, because they occur at different times in the two coils. With a certain size of such a defect, the associated signal voltage exceeds the threshold voltage in the signal voltage threshold stage 26, such that a binary signal is generated at its output 28.

Figure 2A:
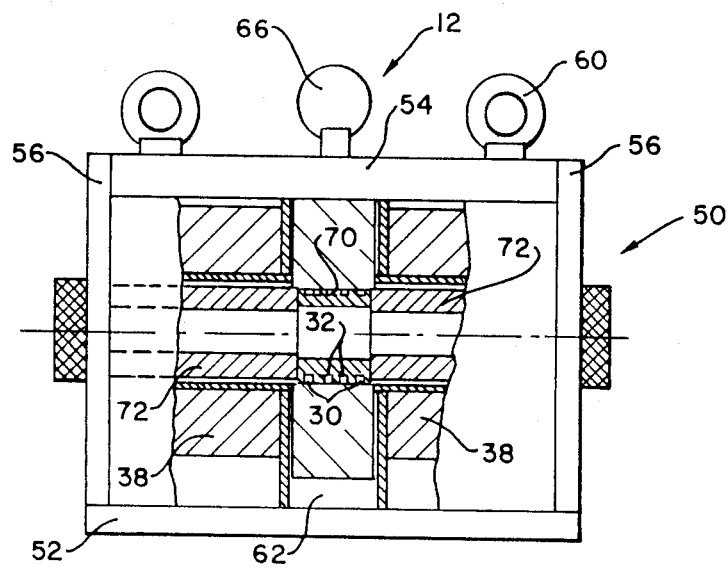
Figure 2B:
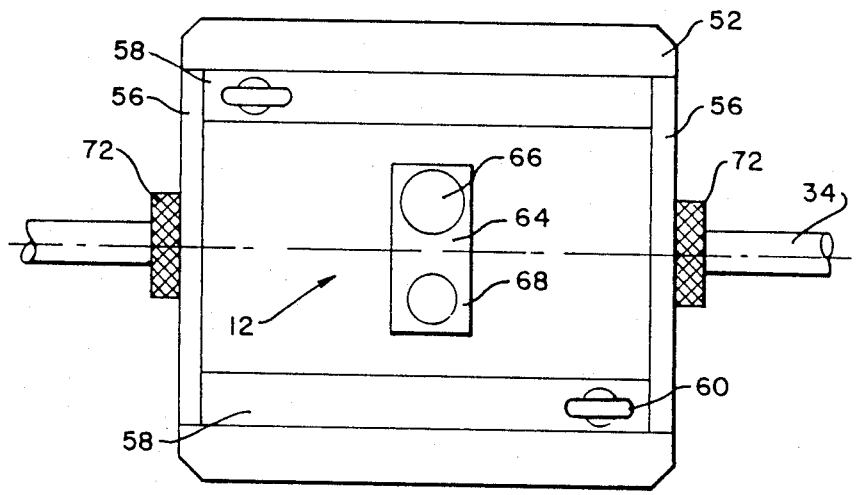
Figure 3:
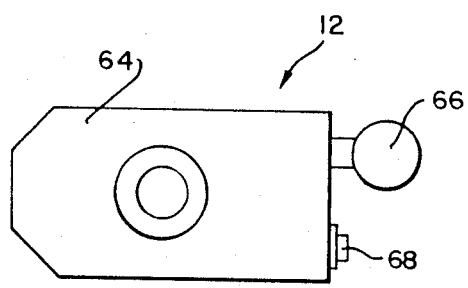
FIG. 3 shows the test coil arrangement.

Construction of the test coil arrangement 12 and of an additional magnetizing yoke 50 serving simultaneously for supporting the test coil arrangement 12 can best be seen from FIGS. 2a, 2b and 3. FIGS. 2a and 2b show the magnetizing yoke 50 with built-in test coil arrangment 12 in partially sectional view and in top view, respectively, while FIG. 3 shows the test coil arrangement 12 separately in a side view. The case of the magnetizing yoke 50 is composed of a bottom plate 52, a top plate 54, two side plates 56 and two wall plates 58, each made of a ferromagnetic material. Two carrying lugs 60 fastened to the top plate 54 serve for manual transportation.

On either side of an opening 62, two magnetizing coils 38 are arranged, these coils being connected in series and to a direct-current supply 36 (FIG. 1). The test coil arrangement 12 is inserted into the opening 62 which is extended by a cutout of the top plate 54. The test coil arrangements consists of a case 64, a handle 66, a terminal socket 68 and a coil carrier 70 with four winding grooves therein, into which the exciter coils 30 and the receiver coils 32 are embedded. These coils are connected with each other as described, and are connected over the terminal socket 68 and a cable (not shown) to the generator 10 or the input of the amplifier 18, respectively.

Into the central openings of the coils 38, exchangeable guide nozzles 72 of ferromagnetic material are inserted, and which serve two purposes. First, they are intended to guide the wire 34 to be tested and to protect in that way the borehole of the coil carrier 70 against wear and damage. For this purpose, they are available in different diameters corresponding to the respective diameter of the wire 34. Secondly, they guide the magnetic flux produced by the magnetic field of the coils 38 in connection with the ferromagnetic plates 52 to 58 in an optimum way into the ambit of the coils 32.

Receiver coils 32 have, beside their purpose as eddy current coils described above, still another purpose. The ferromagnetic particles that may be included in the wire 34 and which pass through the coils 32 are magnetized by the magnetic field of the magnetizing coils 38 and cause changes in the magnetic flux inducing a signal voltage in the coils 32. In principle, a simple coil 32 is sufficient for this. However, using two coils constructed identically, but connected in difference is advantageous in that voltages caused by interference fields, e.g. interference fields in the power supply, compensate each other in the two coils 32. Ferromagnetic particles induce, in analogous manner to the eddy-current signal voltages, at different times in the two coils 32 signal voltages of opposite polarity appearing as composite signal voltages at the terminals 16.

Instead of the magnetizing yoke 50 with two magnetizing coils 38 and the direct-current supply 36, a magnetizing yoke with one or several permanent magnets for generating the necessary constant magnetic field may be employed. It is advantageous, herein, to use such magnetizing yokes which will effect magnetic saturation of ferromagnetic test samples during test, if it is desired to overcome the influence of the magnetic permeability by magnetic saturation.

The signal voltages at the terminals 16 of the test coil arrangement 12, i.e. those caused by eddy currents as well as those caused by D.C. energization, are amplified commonly in the preamplifier 18. The output of the preamplifier 18 is connected with the input of a low-pass filter 40, the latter being designed such that remainders of the carrier frequency of the generator 10 are completely suppressed. For this purpose, the low pass filter 40 is convertible in its limit frequency. The conversion takes place, as shown by the broken line 41, coupled with the conversion of the test frequency of the generator 10, such that for a selected test frequency, simultaneously the matching limit frequency of the low-pass filter 40 is adjusted, too. To the output of the low-pass filter 40, an amplifier 42 is connected, the output of which, in turn, interconnects with a signal voltage threshold stage 44. When the signal voltage exceeds a given value at the output 46 of the signal voltage threshold stage 44, a binary signal is generated. This is intended to indicate that the test coil arrangement 12 has been passed by a ferromagnetic inclusion in the wire 34.

A signal at the output 28 of the eddy current channel indicates that an inhomogeneity (defect) at the surface of the wire 34 has passed the test coil 32. This may also have been, of course, a particle of ferromagnetic material contacting the surface of the wire 34. In contrast, a signal at output 46 of the induction channel indicates that solely a ferromagnetic particle, irrespective if on or under the surface of the wire 34, has passed the test coil.

The signals at the two outputs 28, 46 can be evaluated in different manner. A counting of the signals per wire bundle and/or per unit length may be peformed. A color marking of defective locations of both categories is possible, as well as the application of acoustic or optical signaling devices. Due to the large amount of data eventually occurring, computer based processing seems reasonable, in particular when the combination of the signals of both outputs 28 and 46 is concerned.

A simple processing circuit for handling a combination of the two signals is shown in FIG. 1. The outputs 28 and 46 are connected to the two inputs of an AND gate 74 and with one input of the AND gates 76, 78 each. Another input each of the two AND gates 76, 78 is connected over an inverter 80 to the output of the AND gate 74. Thus, three further outputs 82, 84, 86 result. A signal occurs at the output 82, if there is one solely at output 28, i.e. if the indicated defect consists only in a material separation or inhomogeneity of the wire surface, not in the presence of a ferromagnetic particle. A signal at output 86 indicates that there is a signal solely at output 46, i.e. that a ferromagnetic inclusion underneath the wire surface is signaled. If a signal appears at output 84, this indicates that a ferromagnetic particle with surface contact has passed the test coil 12. It can be found, therefore, that a very simple combination of the signals of the eddy-current and of the induction channel readily lead to differentiated information as to the kinds of defects detected by the apparatus.

What is claimed is:

1. A device for defect testing of non-ferromagnetic test samples and for the presence of ferromagnetic inclusions in said test samples, comprising:
    means for inducing alternating eddy currents in the test samples including a coil arrangement energized by a selectively variable alternating current generator;

a permanent magnet yoke of such strength as to produce magnetic saturation of ferromagnetic samples for inducing a constant D.C field in the test samples at the same time as the alternating eddy currents;

receiver coil means including two spaced apart differentially connected receiver coils coupled to the test samples for developing a first signal corresponding to the reaction of alternating eddy currents with the non-ferromagnetic test samples and a second signal corresponding to a reaction of the D.C. field in the test samples with a ferromagnetic inclusion, said first and second signals existing in composite form;

a first thresholded circuit connected to the receiver coil means for producing a third signal responsive to the first signal indicating the presence of a physical defect in the non-ferromagnetic test sample;

a second thresholded circuit including a low-pass filter connected to the receiver coil means for preventing passage of the first signal and for producing a fourth signal responsive to the second signal to indicate the presence of a ferromagnetic inclusion in the test samples, said low-pass filter being variable in common with the current generator;

a preamplifier interconnected between the receiver coil means and the first and second circuits;

a logic circuit fed by both the third and fourth signals for producing a fifth signal indicating the presence of both the third and fourth signals; and means responsive to said third, fourth and fifth signals for providing sixth, seventh and eighth signals indicative of, respectively, the existence of a defect only in a material separation or inhomogeneity of the surface of the sample not in the presence of a ferromagneetic inclusion, the existence of a ferromagnetic inclusion underneath the sample surface, and the existence of a ferromagnetic inclusion with surface contact.

* * * * *